:::

United States Patent [19]
Lohr, Jr. et al.

[11] Patent Number: 5,959,126
[45] Date of Patent: Sep. 28, 1999

[54] FORMATION OF QUINONEDIMINES FROM PHENYLENEDIAMINES BY CATALYTIC OXIDATION

[75] Inventors: Raymond Anton Lohr, Jr., Avon; Otto William Maender; Donald Lee Fields, Jr., both of Copley, all of Ohio

[73] Assignee: Flexsys America L. P., Akron, Ohio

[21] Appl. No.: 09/022,671

[22] Filed: Feb. 12, 1998

Related U.S. Application Data

[60] Provisional application No. 60/063,764, Oct. 29, 1997.

[51] Int. Cl.$^6$ ................................................. C07C 249/02
[52] U.S. Cl. .......................... 552/301; 552/302; 564/248; 564/277
[58] Field of Search ..................................... 564/277, 248; 552/301, 302

[56] References Cited

U.S. PATENT DOCUMENTS

| | | | |
|---|---|---|---|
| 2,118,826 | 5/1938 | Semon | 260/56 |
| 4,264,776 | 4/1981 | Hershman et al. | 564/384 |
| 4,624,937 | 11/1986 | Chou | 502/180 |
| 4,696,772 | 9/1987 | Chou | 260/502.5 F |
| 5,091,545 | 2/1992 | Parker | 552/302 |
| 5,118,807 | 6/1992 | Wheeler | 544/197 |
| 5,189,218 | 2/1993 | Desmurs et al. | 564/272 |
| 5,208,280 | 5/1993 | Wheeler | 524/100 |
| 5,371,289 | 12/1994 | Cottman et al. | 564/396 |
| 5,672,725 | 9/1997 | Polis | 552/293 |

FOREIGN PATENT DOCUMENTS

| | | |
|---|---|---|
| 162035 | 11/1985 | European Pat. Off. . |
| 708080 | 4/1996 | European Pat. Off. . |
| 708081 | 4/1996 | European Pat. Off. . |
| 2659651 | 3/1991 | France . |
| 2659650 | 9/1991 | France . |

*Primary Examiner*—Peter O'Sullivan
*Attorney, Agent, or Firm*—Louis A. Morris

[57] ABSTRACT

A phenylenediamine compound can be converted, with high selectivity, into its corresponding quinonediimine by reacting the phenylenediamine with oxygen in the presence of a modified activated carbon catalyst in an aqueous system.

28 Claims, No Drawings

FORMATION OF QUINONEDIIMINES FROM PHENYLENEDIAMINES BY CATALYTIC OXIDATION

This application claims priority to the filing date of U.S. Provisional Application 60/063,764, filed Oct. 29, 1997.

FIELD OF THE INVENTION

This invention relates to a process for the preparing quinonediimines from their corresponding phenylenediamines using an activated carbon catalyst which has had surface oxides removed therefrom.

BACKGROUND OF THE INVENTION

The class of cyclic enones is well known in organic chemistry. Best known examples of cyclic enones are quinones such as, for example, the benzoquinones, naphthoquinones, anthraquinones, phenanthraquinones, and the like. 1,4-Benzoquinone is commonly referred to as quinone. Quinones are generally brightly colored compounds and have versatile applications in chemical synthesis, biological uses, as redox materials, as well as in industry. There are several review articles on the chemistry and applications of quinones including, for example, *Kirk-Othmer Encyclopedia of Chemical Technology*, Third ed., Vol. 19, pages 572–605, John Wiley & Sons, New York, 1982.

The synthesis of quinones is well documented. See, for example, J. Cason, *Synthesis of Benzoquinones by Oxidation*, in *Organic Synthesis*, Vol. IV, page 305, John Wiley & Sons, New York (1948). Quinones generally are prepared by oxidizing the appropriately disubstituted aromatic hydrocarbon derivatives, the substituents being hydroxyl or amino groups in the ortho or para positions. 1,4-Benzoquinone, for example, can be made from the oxidation of hydroquinone, p-aminophenol or p-phenylenediamine, or sometimes from quinic acid. The reagents generally used for the oxidation are dichromate/sulfuric acid mixture, ferric chloride, silver (II) oxide, or ceric ammonium nitrate. In these cases, oxidation of the aminoaromatic compound is accompanied by hydrolysis to the corresponding quinone. Some processes may also take several hours for completion of the reaction.

Thus, some of the prior art processes utilize a catalytic agent to achieve an acceptable reaction rate while other processes proceed without catalysts. The process according to the present invention utilizes a catalyst which provides high conversion and reaction rates to prepare the quinonediimine.

A prior art process which utilizes a catalyst in the preparation of a quinoneimine compound is disclosed by Desmurs, et al. in U.S. Pat. No. 5,189,218. The process of Desmurs, et al., which converts a N-(4-hydroxyphenyl) aniline into N-phenylbenzoquinone-imine, utilizes a manganese, copper, cobalt, and/or nickel compound as a catalyst in an oxidation type reaction.

Other processes are known which use oxidizing agents to convert phenylenediamines into their corresponding quinonediimines in the absence of any catalytic agent. Such processes are described by Wheeler in U.S. Pat. No. 5,118,807 and by Haas et al, in EP 708,080.

The above process of Desmurs, et al., which uses a metal catalytic component, along with any other processes which utilize a metal catalyst, have several drawbacks. Not only are the metal catalysts relatively expensive, they raise important environmental concerns. For example, effluent streams and products can be contaminated by the metals. Further, recovery of the catalyst for reuse can be prohibitively expensive.

Various non-heavy metal catalysts are known in the art. For example, activated carbon catalysts, which are typically prepared by heating carbon to high temperatures (800° C. to 900° C.) with steam or with carbon dioxide to bring about a porous particulate structure and increased surface area, are well known oxidation catalysts. U.S. Pat. No. 4,264,776, for example, discloses and claims a process for preparing secondary amines by catalytic oxidation of tertiary amines using an activated carbon catalyst.

U.S. Pat. No. 4,158,643 teaches a method for oxidation modification of an activated carbon support in which oxygen is added to the surface of the activated carbon, and then the carbon support is impregnated with an inert hydrophobic compound. The carbon support, which may be any commercially available activated carbon for vapor phase activation use, is useful in oxidizing carbon monoxide in the presence of sulfur dioxide for an extended period of time.

U.S. Pat. No. 4,624,937 provides a method for preparing activated carbon for catalytically oxidizing tertiary amines or secondary amines in the presence of oxygen or an oxygen-containing gas to selectively produce secondary or primary amines. The method of U.S. Pat. No. 4,624,937 comprises the step of treating the carbon catalyst to remove oxides from the surface thereof.

Thus, it can be seen that processes for preparing diimines from diamines are known. Additionally, the use of various carbon catalysts, including activated carbon, in chemical reactions is known. However, the use of a modified activated carbon compound as a catalyst in the conversion of diamino compounds to give highly selective yields of diimino compounds has not heretofore been suggested.

SUMMARY OF THE INVENTION

It has been discovered that a phenylenediamine compound can be converted into its corresponding quinonediimine by reacting the phenylenediamine with oxygen in the presence of a modified activated carbon catalyst.

The modified activated carbon catalyst of the present invention has been treated to remove oxides from the surface thereof. Such a modified carbon catalyst allows the conversion of phenylenediamine to quinonediimine in an almost quantitative (HPLC) yield.

In contrast to prior art, an advantage of the present invention is that the conversion of phenylenediamine to the corresponding quinonediimine is nearly quantitative. Thus, very little waste material remains upon completion of the reaction.

Another advantage comes from the use of the modified activated carbon catalyst. The modified activated carbon catalyst not only is recyclable, but also avoids the drawbacks associated with metal catalysts which include high cost, product contamination and environmental waste concerns.

An additional advantage is that the modified activated carbon catalysts as set forth herein provide a faster, more complete reaction compared to commercially available activated carbon catalysts in the conversion of diamines to diimines.

Still further advantages of the present invention will become apparent to those skilled in the art upon reading and understanding the following detailed description of the preferred embodiments.

DETAILED DESCRIPTION OF THE INVENTION

The object of the present invention is to provide an effective process for converting phenylenediamines into their corresponding quinonediimines.

In accordance with the object of the invention, a phenylenediamine (ortho or para) according to Formula I:

Formula I

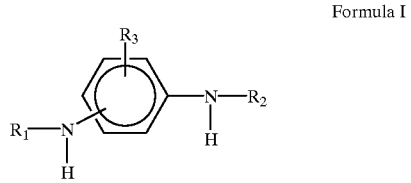

wherein $R_1$, $R_2$ and $R_3$ are the same or different radicals selected from hydrogen, alkyl, aryl, aralkyl, alkaryl, cycloalkyl, heterocycle, acyl, aroyl, carbamyl and cyano is reacted with oxygen in the presence of water and a modified activated carbon catalyst which has had surface oxides removed therefrom. The reaction produces a corresponding quinonediimine according to Formula IIa or IIb:

Formula IIa

Formula IIb

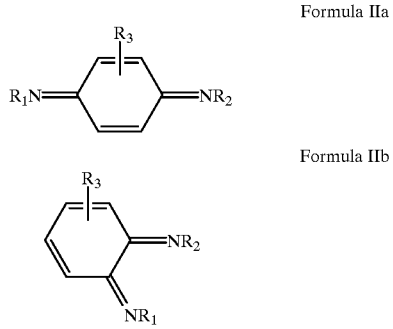

wherein $R_1$, $R_2$ and $R_3$ are the same as in the compound according to Formula I.

The reaction is represented as follows:

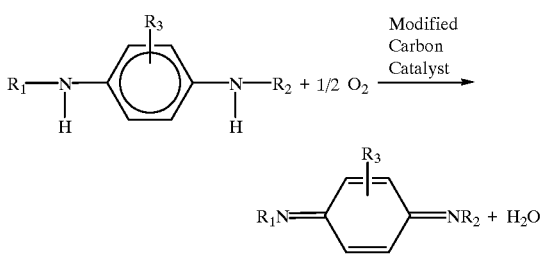

Examples of satisfactory radicals for $R_1$, $R_2$ and $R_3$ are linear or branched alkyls such as methyl, ethyl, propyl, butyl, pentyl, hexyl, heptyl, octyl, nonyl, decyl, dodecyl, and the like; aryls such as phenyl, naphthyl, anthracyl, tolyl, ethylphenyl, and the like; cycloalkyls such as cyclobutyl, cyclopentyl, cyclohexyl, cyclooctyl, and the like. Other examples include allyl and isobutenyl; 1,3,5-sym-triazinyl, 2-benzothiazolyl, 2-benzimidazolyl, 2-benzoxazolyl, 2-pyridyl, 2-pyrimidinyl, 2,5-thiadiazolyl, 2-pyrazinyl, adipyl, glutaryl, succinyl, malonyl, acetyl, acrylyl, methacrylyl, 3-mercaptopropionyl, caproyl, benzoyl, phthaloyl, terephthaloyl, aminocarbonyl, carbethoxy, carbonyl, formyl, and the like. These are merely exemplary radicals and are in no way intended to limit the scope of the invention.

The modified activated carbon catalyst is prepared by removing both acidic and basic surface oxides from the surfaces of a carbon catalyst. A method for making the modified activated carbon catalyst is set forth in U.S. Pat. No. 4,624,937, the disclosure of which is incorporated herein by reference.

According to U.S. Pat. No. 4,624,937, a carbon material such as those described in U.S. Pat. No. 4,264,776, the teachings of which are incorporated herein by reference, is initially provided.

Ordinarily, the carbon catalyst is a commercially available activated carbon with a carbon content ranging from about 10% for bone charcoal to about 98% for some wood chars and nearly 100% for activated carbons derived from organic polymers. The noncarbonaceous matter in commercially available carbon materials will normally vary depending on such factors as precursor origin, processing, and activation method. The treatment process can be accomplished by a single or a multistep scheme which in either case results in an overall chemical reduction of oxides on the carbon surface, i.e., a reduction or removal of acidic oxides from the carbon surface.

As used herein, the term "oxides" is intended to mean carbon functional groups which contain oxygen as well as hetero atom functional groups which contain oxygen. Other hetero atom functional groups which do not contain oxygen may also be removed from the surface of the carbon material during treatment.

In a two-step scheme, the carbon material can be first treated with an oxidizing agent such as, for example, liquid nitric acid, nitrogen dioxide, $CrO_3$, air, oxygen, $H_2O_2$, hypochlorite, or a mixture of gases obtained by vaporizing nitric acid. The treatment can be accomplished using either a gas or a liquid oxidizing agent. Where a liquid is used, concentrated nitric acid containing from about 10 to about 80 g. $HNO_3$ per 100 g. of aqueous solution is preferred. Preferred gaseous oxidants include oxygen, nitrogen dioxide, and nitric acid vapors. A particularly effective oxidant is nitric acid in the vapor phase which includes nitric acid carried into the vapor phase by an entraining gas as well as the vapors obtained by distilling liquid nitric acid. With a liquid oxidant, temperatures from about 60° C. to about 90° C. are appropriate, but with gaseous oxidants, it is often advantageous to use temperatures of about 50° C. to about 500° C. or even higher for the treatment step.

The treatment can be achieved by placing carbon from a manufacturer in a round bottom flask which contains a magnetic stirring bar. Liquid nitric acid is selected as the oxidizing agent for illustration. The amount of carbon used is determined by the percent carbon load desired (% carbon load=g. of carbon used per 100 ml of nitric acid solution) and the nitric acid solution volume to be used. Ordinarily, 1 to 200 g. of carbon per 100 ml of nitric acid or other liquid oxidizing agent is satisfactory. Temperature control can be provided by any suitable means. A condenser and scrubber can be connected to the round bottom flask as desired. A calculated volume of water, preferably deionized water, is added to the carbon, followed by sufficient 69–71% nitric acid to achieve the desired nitric acid solution. The carbon and nitric acid solution are then stirred for the desired period at the desired temperature.

After stirring, the carbon is filtered, and the resulting wet cake may or may not be washed and/or dried prior to pyrolysis.

The time during which the carbon is treated with the oxidant can vary widely from about 5 minutes to about 10 hours. Preferably, a reaction time of about 30 minutes to about 6 hours is satisfactory. When concentrated nitric acid is the oxidant, a contact time of about 30 minutes to about 3 hours is satisfactory.

In a second step, the oxidized carbon material is pyrolyzed, i.e., heat treated, at a temperature in the range of about 500° C. to about 1500° C., preferably from about 800° C. to 1200° C.

It is preferred to conduct the pyrolysis in an inert gas atmosphere, such as nitrogen, argon, or helium.

Wet cake or dry carbon is placed in a ceramic pyrolysis dish which together are placed in a quartz tube. Nitrogen is passed through water at about 70° C., then through the quartz tube during pyrolysis. A dry, static nitrogen atmosphere is maintained after flushing the quartz tube with several tube volumes of dry nitrogen prior to pyrolysis. The quartz tube containing the pyrolysis dish is placed in a suitable pyrolyzer apparatus at about 930° C. for the desired period, followed by cooling while maintaining the nitrogen atmosphere.

Pyrolysis can last anywhere from about 5 minutes to 60 hours, although 10 minutes to 6 hours is normally satisfactory. The shorter times are preferred for economic reasons because, as might be expected, continued exposure of the carbon to elevated temperatures for prolonged periods can result in a poor carbon catalyst for the oxidation. Pyrolysis may be initiated in a slightly moist atmosphere or an atmosphere which contains $NH_3$ as this appears to produce a more active catalyst in a shorter time.

Alternatively, the treatment is accomplished in a single step by pyrolyzing the carbon material as described above while simultaneously passing a gas stream comprised of $NH_3$ and an oxygen-containing gas, e.g., $H_2O/NH_3$, through the carbon. The flow rate of the gas stream should be fast enough to achieve adequate contact between fresh gas reactants and the carbon surface, yet slow enough to prevent excess carbon weight loss and material waste. Many $NH_3$/oxygen-containing gas mixtures can be used such as, for example, $NH_3/CO_2$, $NH_3/O_2$, $NH_3/H_2O$ and $NH_3/NOx$, provided the gas mixture achieves the desired result. Ordinarily, the oxygen-containing gas/$NH_3$ ratio can range from 0:100 to 90:10. Furthermore, nitrogen can be used as a diluent to prevent severe weight loss of the carbon in high oxygen-containing gas concentrations. Ammonia is a basic gas, and, as such, is believed to assist the decomposition of the various oxide groups on the surface of the carbon material. Any other chemical entity which will generate $NH_3$ during pyrolysis should also prove satisfactory as an $NH_3$ source. For economic reasons, an $NH_3/H_2O$ gas stream is most preferred.

The carbon materials treated according to the procedure set forth above, when used in the catalytic oxidation of phenylenediamine to quinonediimine, demonstrates a faster reaction rate than with commercially available activated carbon. Other activated carbons, when used in the reaction in accordance with the present invention, did not give any better reaction rate in conversion of phenylenediamine to the corresponding quinonediimine than when $O_2$ was used without any catalyst present.

The reaction, according to the present invention, takes place in the presence of water. The amount of water present in the system affects the rate of the reaction. The more water present, the faster the reaction. However, there is an upper limit on how much water can be present. If too much water is used, a side reaction occurs which results in the hydrolysis of the quinonediimine to give the N-substituted-benzoquinoneimine according to Formula III.

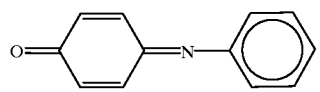

Formula III

Various solvents may be used in the reaction in accordance with the present invention. Examples of solvents which may be used in the reaction according to the present invention include, but are not limited to, ketones, alcohols, nitriles, and aliphatic and/or aromatic hydrocarbon solvents including alkanes and alkenes, halogenated hydrocarbons, and mixtures thereof. Specific examples of solvents useable in the process of the present invention include acetone, cyclohexanone, 5-methyl-2-hexanone, 5-methyl-3-heptanone, methyl alcohol, ethyl alcohol, isopropyl alcohol, methylisobutyl carbinol, acetonitrile, dichloromethane, chloroform, carbontetrachloride, dimethylsulfide, N-methylpyrrolidone, and xylene.

The reaction, according to the present invention may be carried out under varying pH's. Various pH modifying agents can be utilized in accordance with the present invention. These maybe selected from classes of organic acids or nitrogen containing bases. Examples range from acidic pH modifiers such as acetic acid (pH 2.4) to basic pH modifiers such as triethylamine (pH12). Generally, the pH of the system can range from a pH of 2 to a pH of 12. Preferably, the pH range of the system is from 7 to 12.

The reaction of the present invention takes place in an oxygen system. The system is typically reacted from atmospheric to 1500 psig $O_2$. Preferably, the system is between 15 to 100 psig $O_2$. The oxygen concentration can range from 100 to 2% (using nitrogen dilution).

It is also possible to utilize a phase transfer catalyst to accelerate the rate of reaction in the process of the present invention. Phase transfer catalysts useable in the present invention include, but are not limited to, quaternary ammonium salts, phosphonium salts, low molecular weight polyethylene glycols, and crown ethers.

The present invention can be more clearly illustrated by the following examples. Examples 1–4 describe the preparation of para-quinonediimine (QDI) [$R_1$=1,3-dimethylbutyl, $R_2$=phenyl] from the para-phenylenediamine of Formula I [$R_1$=1,3-dimethylbutyl, $R_2$=phenyl] (Santoflex® 6PPD) using a modified activated carbon catalyst. The catalyst was prepared in accordance with the procedure as set forth above.

EXAMPLE 1

A mixture of 5.0 g. of N-1,3-dimethylbutyl-N'-phenyl-p-phenylenediamine (6 PPD), 98.0 g. acetone, 1.0 g. water, 1.0 g. modified activated catalyst and 1.0 g. triethylamine was charged to a 300 ml Parr autoclave. The system was reacted under 30 psig oxygen at 35° C. for one hour at which time no further oxygen consumption could be detected. The autoclave was cooled to room temperature and the mixture was analyzed. This solution had changed color (from a dark brown to an orange) during the reaction time. HPLC analysis revealed 100% conversion to the QDI. The autoclave mixture was filtered to remove the carbon. The QDI was isolated by removing the solvent under vacuum. The air dried carbon weighed 1.4 g. and the QDI (a viscous blood red liquid) weighed 4.7 g.

EXAMPLE 2

A mixture of 50.0 g. of N-1,3-dimethylbutyl-N'-phenyl-p-phenylenediamine (6 PPD), 148.5 g. of methanol, 1.5 g. of water, 5.0 g. of modified activated catalyst and 2.0 g. triethylamine was charged to a 300 ml Parr autoclave. The system was reacted under 30 psig oxygen at 35° C. until oxygen consumption ceased. The HPLC analysis of this reaction batch indicated that all of the charged N-1,3-dimethylbutyl-N'-phenyl-p-phenylenediamine (6 PPD) was converted to QDI. However, there was a new peak (<2%) in the HPLC chromatogram which corresponds to N-phenyl-p-benzoquinoneimine which is formed from the hydrolysis of the diimine. This and the diimine were the only detectable peaks in the chromatogram. The isolated QDI weighed 48.4 g.

EXAMPLE 3

A mixture of 5.0 g. of N-1,3-dimethylbutyl-N'-phenyl-p-phenylenediamine (6 PPD), 90.0 g. of methanol, 10.0 g. of water, 1.0 g. modified activated catalyst and 1.0 g triethylamine was charged to a 300 ml Parr autoclave. The system was reacted under 30 psig oxygen at 35° C. for less than 20 minutes at which time oxygen consumption had ceased. The analysis of this batch revealed no 6 PPD and the desired converted QDI. However, the above-mentioned hydrolysis product represented 10% of the area count of the HPLC chromatogram.

Thus, while increasing the amount of water from 1.0 g. in Example 1 to 10.0 g. in Example 3 decreased the reaction time from 1 hour to less than 20 minutes, there was a corresponding increase in hydrolysis of the QDI.

EXAMPLE 4

A mixture of 250.0 g. N-1,3-dimethylbutyl-N'-phenyl-p-phenylenediamine (6 PPD), 392 g. (495 ml) of methanol, 5.0 g. water, 25.0 g. modified activated catalyst and 5.0 g. triethylamine was charged to a 1000 ml Parr autoclave equipped with an oxygen dip tube fitted with a 10 micron frit for subsurface introduction. The system was reacted under 30 psig oxygen at 50° C. until oxygen consumption ceased. Using this fresh carbon, reaction time was 1 hour. The mixture was cooled to room temperature and the autoclave was sampled and HPLC analyzed. This analysis indicated 98.5% QDI, the remaining 1.5% being the N-phenyl-p-benzoquinoneimine. After catalyst removal by filtration, the solvent was removed under vacuum to give 243 g. of QDI as a residue product To this emptied autoclave another 250 g. of N-1,3-dimethylbutyl-N'-phenyl-p-phenylenediamine (6 PPD), 238 g. (300 ml) of recovered methanol (containing the water and amine), recovered carbon catalyst, and 158 g. (200 ml) of fresh methanol was charged. The system was reacted under 30 psig oxygen at 50° C. until consumption ceased (2.5 hours). The analyzed reaction mixture was 97% QDI and 3% N-phenyl-p-benzoquinoneimine with an isolated yield of 99%.

The above Example 4 demonstrates the ability to re-use the modified carbon catalyst while maintaining high rate and high conversion of diamine to diimine.

EXAMPLE 5

This example shows the criticality of the presence of water in the present reaction system. In the following example, no water is in the system.

A mixture of 5.0 g. of N-1,3-dimethylbutyl-N'-phenyl-p-phenylenediamine (6 PPD), 99.0 g. acetone 1.0 g. modified activated carbon catalyst and 1.0 g. of triethylamine was placed in a 300 ml Parr autoclave. The system was reacted under 30 psig oxygen at 35° C. for several hours with no observed consumption of oxygen. After this time, the contents of the autoclave was cooled to room temperature and analyzed by HPLC. This analysis indicated that <4% of the charged 6 PPD was converted to the desired QDI.

EXAMPLE 6

The following example describes the preparation of para-quinonediimine [$R_1$=$R_2$=1,4-dimethylpentyl] from para-phenylenediamine [$R_1$=$R_2$=1,4-dimethylpentyl] (Santoflex® 77 PD) using the above mentioned carbon catalyst.

A mixture of 15.0 g. of N,N'-di-(1,4-dimethylpentyl)-p-phenylenediamine (77 PD), 98.0 g. acetone, 1.0 g. water, 2.5 g. modified activated catalyst and 1.0 g. triethylamine was charged to a 300 ml Parr autoclave. The system was reacted under 35 psig oxygen at 45° C. until no further oxygen consumption could be detected. The autoclave was cooled to room temperature, filtered to remove the carbon catalyst and the solvent was removed under vacuum. While the starting material was a liquid, the isolated product (14.3 g.) was a soft waxy solid (m.p. 62–66° C.). HPLC analysis revealed that 0.65% of the starting material remained in this sample. The chromatogram also separated the geometric isomers of this quinonediimine.

EXAMPLE 7

The following example describes the preparation of a mixture of quinonediimines [$R_1$=1,3-dimethylbutyl or 1,4-dimethylpentyl, $R_2$=phenyl] from Santoflex® 134PD using the above mentioned modified carbon catalyst. Santoflex® 134PD is a mixture of N-1,3-dimethylbutyl-N'-phenyl-p-phenylenediamine (33 weight percent) and N-1,4-dimethylpentyl-N'-phenyl-p-phenylenediamine (67 weight percent).

A mixture of 25.1 g. Of Santoflex® 134 PD , 49.0 g. methanol, 0.5 g. water, 2.5 g. modified carbon catalyst and 0.5 g. trimethylamine was charged to a 300 ml Parr autoclave. The system was reacted under 30 psig oxygen at 45° C. for 30 mins. at which time no further oxygen consumption could be detected. The autoclave was cooled, filtered to remove the carbon catalyst (which was washed with two 10.0 g. methanol solvent washes) and the combined solvent was removed under vacuum. The isolated product weighed 24.2 g. and the carbon catalyst weighed 3.5 g. after being dried at room temperature for 24 hours. HPLC analysis revealed complete conversion of the starting materials with less than 1% of the hydrolysis product (N-phenyl-p-benzoquinoneimine) being formed during the reaction and isolation of the product. The HPLC (Beckman column part no. 235392 ODS C-18) separated the quinonediimines into their geometric isomers.

Other para-phenylenediamines, including Santoflex® IPPD, [$R_1$=phenyl, $R_2$=isopropyl], Santoflex® 44 PD [$R_1$=$R_2$=sec-butyl], 4-aminodiphenylamine [$R_1$=H, $R_2$=phenyl], N,N'-diphenyl-para-phenylenedianine [$R_1$=$R_2$=phenyl] and N-cyclohexyl-N'-phenyl-para-phenylenediamine [$R_1$=cyclohexyl, $R_2$=phenyl] have also been successfully converted to the corresponding quinonediimine according to process of the present invention.

Quinonediimines exhibit multiple activity in vulcanized elastomers. These activities include long term antioxidant activity, along with antiozonant capacity. In fact, the antioxidant capacity of these antidegradants persists even after the vulcanizate has been extracted with solvents. In addition, quinonediimines provide these benefits without the negative effect on scorch generally associated with para-phenylenediamine antidegradants common to the industry. Summary of the activities of these compounds in rubber can be found in the literature. (Cain, M. E. et al., *Rubber Industry*, 216–226, 1975).

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the invention, it is claimed:

1. A highly selective process for preparing a quinonediimine by reacting the corresponding phenylenediamine with oxygen in the presence of a modified activated carbon catalyst, said modified activated carbon catalyst characterized by having the oxides removed from its surface, said reaction further characterized in that it is carried out in the presence of water.

2. A process of claim 1 wherein the oxides are removed from the modified activated carbon catalyst surface by subjecting activated carbon to an oxidizing agent and then pyrolizing the activated carbon in an oxygen free atmosphere at a temperature in the range of about 500° C. to about 1500° C.

3. A process of claim 1 wherein the oxides are removed from the activated carbon catalyst surface by simultaneously pyrolizing the activated carbon in the presence of $NH_3$ and an oxygen containing gas that reacts with the oxides on the surface of the activated carbon at pyrolizing temperatures of about 500° C. to about 1500° C.

4. The process of claim 1 wherein the phenylenediamine is an ortho- or para-phenylenediamine of the following Formula I:

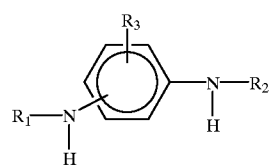

wherein $R_1$, $R_2$ and $R_3$ are the same or different and are selected from hydrogen, alkyl, aryl, aralkyl, alkaryl, cycloalkyl, heterocycle, acyl, aroyl, carbamyl and cyano, and further wherein the resulting corresponding quinonediimine is of the following Formula IIa or IIb:

Formula IIa

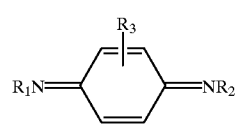

Formula IIb

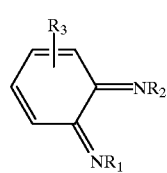

wherein $R_1$, $R_2$ and $R_3$ are the same as in the compound of Formula I.

5. The process of claim 4 wherein $R_1$=1,3-dimethylbutyl, $R_2$=phenyl and $R_3$=hydrogen.

6. The process of claim 4 wherein the compound of Formula I is N-1,3-dimethylbutyl-N'-phenyl-p-phenylenediamine.

7. The process of claim 4 wherein the phenylenediamine is a para-phenylenediamine.

8. The process of claim 7 wherein $R_1$ and $R_2$=1,4-dimethylpentyl and $R_3$=hydrogen.

9. The process of claim 7 wherein $R_1$, $R_2$ and $R_3$ are selected from isopropyl, sec-butyl, cyclohexyl, phenyl and hydrogen.

10. The process of claim 1 wherein the reaction takes place in the presence of a solvent.

11. The process of claim 10 wherein the solvent is selected from ketones, alcohols, nitriles, and aliphatic and/or aromatic hydrocarbon solvents including alkanes and alkenes, halogenated hydrocarbons, and mixtures thereof.

12. The process of claim 11 wherein the alcohol is methyl, ethyl, or isopropyl alcohol.

13. The process of claim 1 which further contains an acidic or basic pH adjusting agent.

14. The process of claim 13 wherein the pH adjusting agent is acetic acid.

15. The process of claim 13 wherein the pH adjusting agent is triethylamine.

16. The process of claim 1 further comprising adding a phase transfer catalyst to the reaction to increase the reaction rate.

17. A process for preparing a quinonediimine from a corresponding phenylenediamine wherein the phenylenediamine is an ortho- or para-phenylenediamine of the following Formula I:

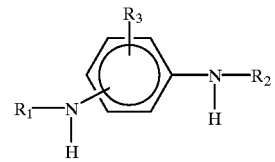

wherein $R_1$, $R_2$ and $R_3$ are the same or different and are selected from hydrogen, alkyl, aryl, aralkyl, alkaryl, cycloalkyl, heterocycle, acyl, aroyl, carbamyl and cyano and further wherein the resulting quinonediimine is of the following Formula IIa or IIb:

Formula IIa

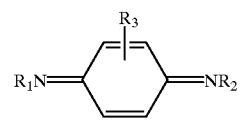

Formula IIb

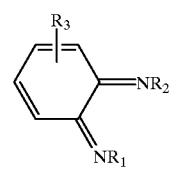

wherein $R_1$, $R_2$ and $R_3$ are the same as in the compound of Formula I; the reaction taking place by combining at least one compound of Formula I with oxygen in the presence of a modified activated carbon catalyst wherein said catalyst comprises activated carbon which has had oxides removed from its surface, the reaction further taking place in an aqueous system.

18. The process according to claim 17 wherein a solvent is further present in the aqueous system.

19. The process of claim 18 wherein the solvent is selected from ketones, alcohols, nitrites, and aliphatic and/or aromatic hydrocarbon solvents including alkanes and alkenes, halogenated hydrocarbons, and mixtures thereof.

20. The process of claim 17 wherein the phenylenediamine is a para-phenylenediamine.

21. The process of claim 20 wherein $R_1$=1,3-dimethylbutyl, $R_2$=phenyl and $R_3$=hydrogen.

22. The process of claim 20 wherein $R_1$ and $R_2$=1,4 dimethylpentyl and $R_3$=hydrogen.

23. The process of claim 20 wherein $R_1$, $R_2$ and $R_3$ are selected from isopropyl, sec-butyl, cyclohexyl, phenyl and hydrogen.

24. The process according to claim 17 wherein the phenylenediamine component is comprised of a mixture of two or more phenylenediamines.

25. The process of claim 24 wherein the phenylenediamine mixture is a mixture of N-1,3-dimethylbutyl-N'-phenyl-p-phenylenediamine and N-1,4-dimethylpentyl-N'-phenyl-p-phenylenediamine.

26. The process according to claim 17 wherein an acidic or basic pH adjusting is further present in the aqueous system.

27. The process according to claim 26 wherein the acidic pH adjusting agent is acetic acid.

28. The process according to claim 26 wherein the basic pH adjusting agent is triethylamine.

* * * * *

UNITED STATES PATENT AND TRADEMARK OFFICE
CERTIFICATE OF CORRECTION

PATENT NO. : 5,959,126
DATED : September 28, 1999
INVENTOR(S) : LOHR, Jr., et al.

It is certified that error appears in the above-indentified patent and that said Letters Patent is hereby corrected as shown below:

On the title page, item [54], and column 1:

Please change "QUINONEDIMINES" to --QUINONEDIIMINES--.

Signed and Sealed this

Eighteenth Day of April, 2000

Attest:

Q. TODD DICKINSON

Attesting Officer

Director of Patents and Trademarks